United States Patent
Rump

[11] Patent Number: 6,004,201
[45] Date of Patent: Dec. 21, 1999

[54] SENSOR ASSEMBLY FOR CONTROLLING THE VENTILATION OF INDOOR SPACES

[75] Inventor: Hanns Rump, Hausen, Germany

[73] Assignee: I.T.V.I. International Techno Venture Invest Aktiengesellschaft, Vaduz, Liechtenstein

[21] Appl. No.: 08/930,528

[22] PCT Filed: Apr. 18, 1996

[86] PCT No.: PCT/EP96/01609

§ 371 Date: Oct. 17, 1997

§ 102(e) Date: Oct. 17, 1997

[87] PCT Pub. No.: WO96/35115

PCT Pub. Date: Nov. 7, 1996

[30] Foreign Application Priority Data

Apr. 29, 1995 [DE] Germany .......................... 195 15 886

[51] Int. Cl.[6] .................................................. B60H 1/24
[52] U.S. Cl. .......................................... 454/75; 73/23.31
[58] Field of Search .................... 454/75, 139; 73/23.31, 73/25.03, 31.02; 422/94, 98

[56] References Cited

U.S. PATENT DOCUMENTS

| | | | |
|---|---|---|---|
| 4,992,965 | 2/1991 | Holter et al. | 454/75 |
| 5,062,065 | 10/1991 | Lampe | 454/75 |
| 5,217,692 | 6/1993 | Rump et al. | 73/25.03 X |
| 5,320,577 | 6/1994 | Tooru et al. | 454/75 |

FOREIGN PATENT DOCUMENTS

| | | |
|---|---|---|
| 35 14 588 | 10/1986 | Germany . |
| 35 25 774 | 1/1987 | Germany . |
| WO 88/02704 | 4/1988 | WIPO . |

OTHER PUBLICATIONS

JP2126146, May 15, 1990, *Patent Abstracts of Japan*.

*Primary Examiner*—Harold Joyce
*Attorney, Agent, or Firm*—Herbert Dubno; Andrew Wilford

[57] ABSTRACT

A pair of pollution sensors which react oppositely to exposure to respective different pollutants are connected together in one or more voltage-divider circuits so that a combined output voltage always becomes either more negative or more positive regardless of which sensor is responding to the presence of the respective pollutant. For example, a tin-dioxide sensor for gasoline exhaust and a tungsten-trioxide sensor for diesel exhaust can be connected in series as a voltage divider with a center tap connected to an evaluating circuit.

5 Claims, 2 Drawing Sheets

SENSOR ASSEMBLY FOR CONTROLLING THE VENTILATION OF INDOOR SPACES

It has been suggested to control the ventilation of motor vehicles such that, whenever the vehicle goes through a zone of elevated pollution level, the system switches from admitting outside air to recirculating interior air.

BACKGROUND OF THE INVENTION

The appropriate sensor system thus determines the pollutant content of the outside atmosphere and operates the ventilation control flap as described above.

See also: DE 3,304,324

Wo 88/02,704

DE 3,731,754,

DE 3,526,462,

P 3,665,044.7-08, and

EP 0,221,971.

Since standard systems only use a single sensor element, e.g. tin-dioxide sensors, only oxidizing gases (carbon monoxide, hydrocarbons) in the exhaust, can be detected while the system is relatively insensitive to diesel exhaust gases (nitrogen oxide, sulfur dioxide, aromatics).

For this reason systems with two sensors have been proposed. One of the sensors (e.g. tungsten trioxide) is provided for diesel exhaust and another sensor (e.g. tin dioxide) for gasoline exhaust. Each sensor is provided on its own signal pad. Each sensor has its own analog/digital convertor which transmits the respective output signals to a central controller (e.g. a microprocessor).

Although the functioning of such two-sensor systems does meet requirements, the two-channel signal evaluation entails relatively high costs.

OBJECT OF THE INVENTION

It is an object of this invention to reduce costs and expense by using single-channel processing.

Figure 4:
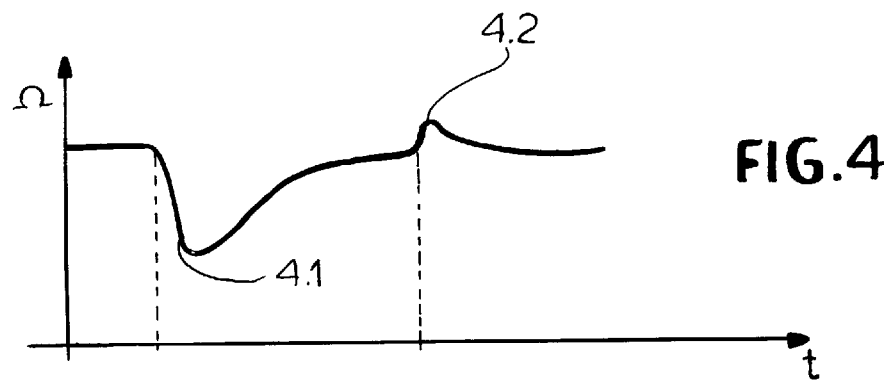
FIGS. 4 and 5 are diagrams illustrating the response of sensors according to the invention.

To this end the invention is basehd on the following observations:

FIG. 4 shows the typical signal curve of a tin-dioxide sensor that is exposed first to gasoline exhaust at 4.1 and then to diesel exhaust at 4.2. The exposure to gasoline exhaust substantially reduces the resistance of the sensor. The exposure to diesel exhaust slightly increases the resistance of the sensor.

Figure 5:
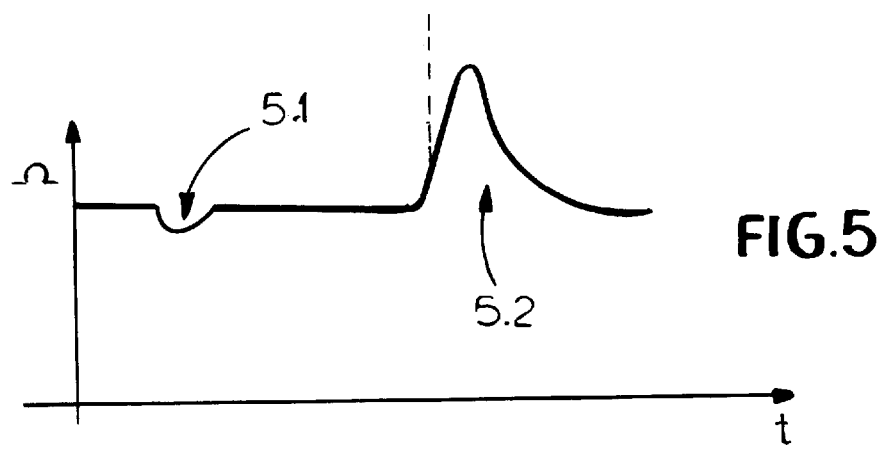

FIG. 5 shows the typical signal curve of a tungsten trioxide sensor that is exposed at 5.1 to gasoline exhaust and later at 5.2 to diesel exhaust. The exposure to gasoline exhaust reduces the sensor resistance slightly. The exposure to diesel exhaust increases the sensor resistance substantially.

Practice shows that both gas groups are almost never found at the same time in homogenous stoichiometric mixtures in street traffic. Instead short gas pulses of different type reach the sensor one after another.

Figure 1:
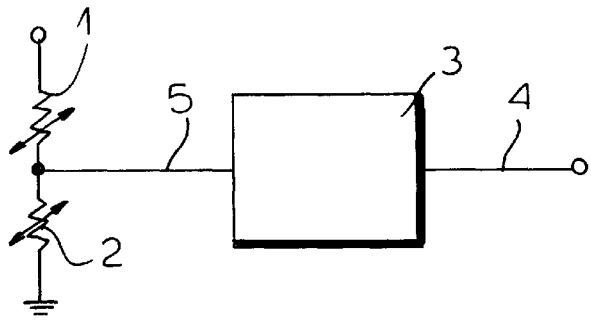
FIG. 1 is a simplified schematic diagram illustrating the invention.

The invention thus proposes a main setup corresponding to FIG. 1. A tin-dioxide sensor 1 is connected as a voltage divider with a tungsten-trioxide sensor 2. The voltage-divider output 5 is fed to a signal processor 3. Its output signal 4 controls the ventilation flap. Since the diesel- and gasoline-containing gas pulses encounter the sensors one after the other, either the sensor 1 is at low ohmage (gasoline exhaust) or the sensor 2 is at high ohmage due to the presence of diesel exhaust. In either case a positive voltage pulse is seen on the voltage divider. If the sensors are switched, of course a negative voltage pulse is seen.

Preferably the voltage-divider output is processed as a single channel which substantially reduces costs.

Figure 6:
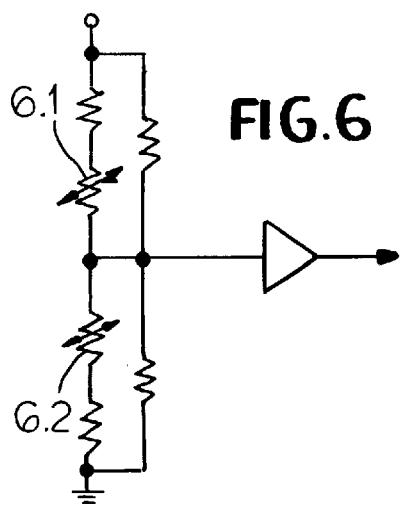
FIGS. 6 and 7 are schematic diagrams of further systems according to the invention.

In order to accommodate the different characteristics to physiological requirements, each sensor is as shown in FIG. 6 connected with a series and a parallel resistor. In this manner diesel exhaust at the same initial concentration produces a voltage pulse some 20 to 40 times greater.

Figure 2:
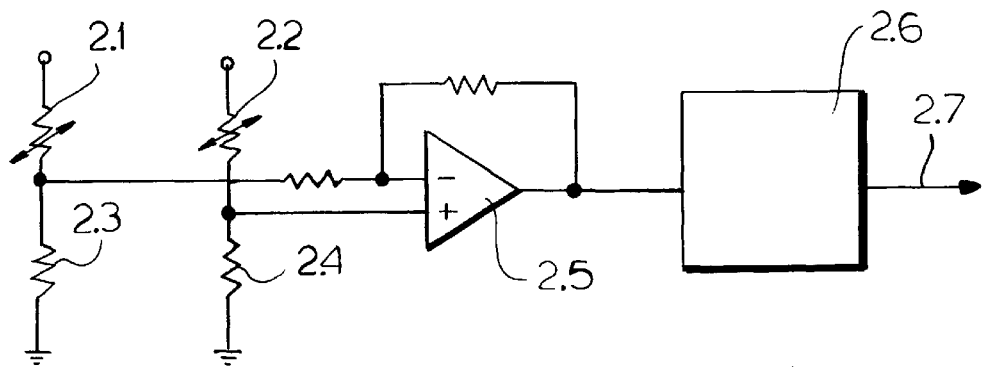
FIGS. 2 and 3 are schematics of circuits embodying the invention.

FIG. 2 shows a variant whereby the sensors each form a voltage divider with an ohmic resistance. The voltage-divider outputs are added in an operational amplifier 2.5 so that its output produces a gas-dependent voltage pulse that always goes in the correct direction independent of the nature of the detected gas.

Figure 3:
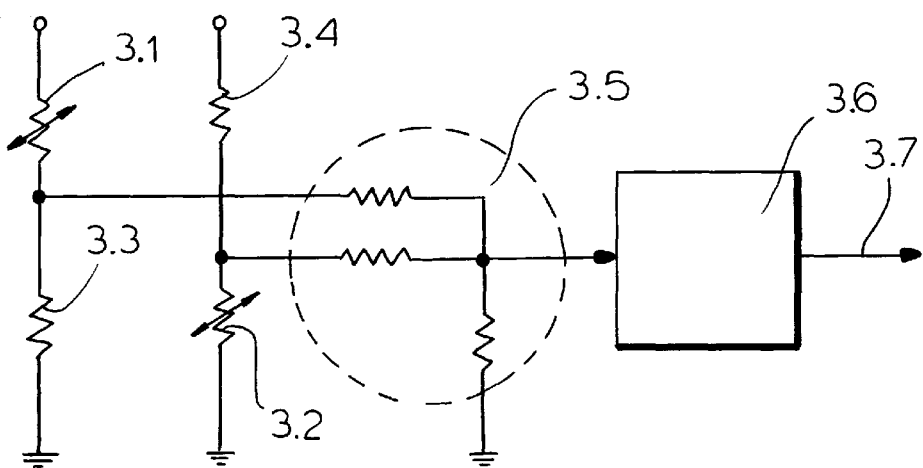

FIG. 3 shows a further variant whereby the sensors are in the respective upper and lower legs of a voltage divider. The two voltage-divider outputs are added at 3.5.

Further embodiments can be postulated in which the two sensors are so connected that the tendency of the resistance change of the two sensors always leads to the same directional change in the voltage output.

It is particularly advantageous to apply the principle of this invention when the sensors and their processing circuitry must be separated from each other. For cost reasons it is often required that the complex signal processing take place in the climate-control system of the vehicle while the sensors are mounted remotely.

To this end preferably a single substrate is provided with a common heater as well as a tin-oxide sensor and a tungsten-trioxide sensor.

Figure 7:
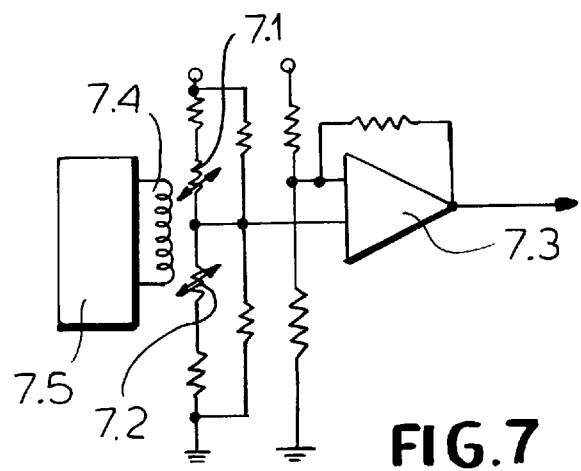

This sensor combination is shown integrated in a circuit in FIG. 7 where the divider voltage is subjected to an impedance change in an operational amplifier 7.3. An electronic control circuit 7.4 supplies the resistance heater 7.5 such that it stays at the same temperature regardless of outside temperature and any air blowing over it.

The combined signal of both sensors is fed via a single electrical line to the control circuitry.

Of course if necessary according to the invention the same goal can be achieved with two separate sensors.

Although in the text only the sensitive metallic oxides of tin oxide and tungsten trioxide are mentioned, of course other metallic oxides are equally usable, as e.g. ZnO, SnxMyOz, TixMy, Oz, $IN_2O_3$, ITO so long as the sensors sensitive to both gas groups are connected such that a voltage or impedance curve varies in the same direction and is correspondingly processed in a signal-processing stage.

What is claimed is:

1. An apparatus for controlling ventilation of a motor-vehicle passenger compartment, the apparatus comprising:

diesel-exhaust sensor means for producing an electrical signal having a resistance that changes in a predetermined direction on detection of diesel exhaust;

gasoline-exhaust sensor means for producing an electrical signal having a resistance that changes in an opposite direction on detection of gasoline exhaust; and circuit means oppositely interconnecting the sensor means for forming an electrical output that changes in a predetermined direction on detection of diesel exhaust by the diesel-exhaust sensor means and on detection of gasoline exhaust by the gasoline-exhaust sensor means.

2. The ventilation-control apparatus defined in claim 1 wherein the circuit means includes respective resistors connected as a voltage divider subtracting the signals from each other.

3. The ventilation-control apparatus defined in claim 1 wherein the circuit means includes respective resistors connected as a voltage divider adding the signals from each other.

4. The ventilation-control apparatues defined in claim 1 wherein the circuit means includes respective resistors in parallel and series with each of the sensor means.

5. The ventilation-control apparatus defined in claim 1 wherein the gasoline-exhaust sensor means includes a tin-dioxide sensor and the diesel-exhaust sensor means includes a tungsten trioxide sensor.

* * * * *